United States Patent
Imai

(10) Patent No.: US 9,820,912 B2
(45) Date of Patent: Nov. 21, 2017

(54) BLOOD BAG SYSTEM

(71) Applicant: TERUMO KABUSHIKI KAISHA, Tokyo (JP)

(72) Inventor: Tadashi Imai, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 311 days.

(21) Appl. No.: 14/779,094

(22) PCT Filed: Apr. 5, 2013

(86) PCT No.: PCT/JP2013/060484
§ 371 (c)(1),
(2) Date: Sep. 22, 2015

(87) PCT Pub. No.: WO2014/162592
PCT Pub. Date: Oct. 9, 2014

(65) Prior Publication Data
US 2016/0045394 A1 Feb. 18, 2016

(51) Int. Cl.
*A61B 19/00* (2006.01)
*A61J 1/10* (2006.01)
*A61M 1/02* (2006.01)
*A61M 1/36* (2006.01)

(52) U.S. Cl.
CPC .............. *A61J 1/10* (2013.01); *A61M 1/0209* (2013.01); *A61M 1/3693* (2013.01); *A61M 1/029* (2013.01); *A61M 2205/12* (2013.01)

(58) Field of Classification Search
CPC ........ A61J 1/10; A61M 1/0209; A61M 1/029; A61M 1/3693; A61M 2205/12
USPC .................................................. 604/403–416
See application file for complete search history.

(56) References Cited

U.S. PATENT DOCUMENTS

| 6,910,998 B2 | 6/2005 | Eberle |
| 8,460,267 B2 * | 6/2013 | Hirabuki ............. A61M 1/3693 604/406 |
| 2010/0170858 A1 * | 7/2010 | Eberle ................. A61M 1/3693 210/782 |

FOREIGN PATENT DOCUMENTS

| EP | 1749546 A1 | 2/2007 |
| EP | 2349395 B1 | 7/2013 |
| JP | 02167173 A | 6/1990 |
| JP | 2009542308 A | 12/2009 |
| JP | 2010528740 A | 8/2010 |
| JP | 2012510298 A | 5/2012 |

(Continued)

OTHER PUBLICATIONS

Extended European Search Report and Opinion, EP Application No. 13880921.5, dated Oct. 27, 2016.

(Continued)

Primary Examiner — Philip R Wiest
(74) Attorney, Agent, or Firm — John R. Merkling

(57) ABSTRACT

A blood bag system (10) includes a blood bag (14) to which centrifugal force is provided in a state where whole blood or a blood component is stored, and a first tube (22) that circulates a fluid centrifugally separated from the blood bag (14). The first tube (22) includes an extending portion (112) extending in an approximately perpendicular direction to a centrifugal direction into which the centrifugal force is applied. Further, a branch tube (114) that can store blood existing in the extending portion (112) is provided at a side of the centrifugal direction of the extending portion (112).

8 Claims, 9 Drawing Sheets

(56) References Cited

FOREIGN PATENT DOCUMENTS

| WO | WO2000054825 A1 | 9/2000 |
| WO | WO200800213 A1 | 1/2008 |
| WO | WO2010061863 A1 | 6/2010 |
| WO | WO2010061866 A2 | 6/2010 |

OTHER PUBLICATIONS

State Intellectual Property Office of People's Republic of China, Second Office Action, CN102215884A, dated Mar. 9, 2017, 10 pages.

* cited by examiner

BLOOD BAG SYSTEM

TECHNICAL FIELD

The present invention relates to a blood bag system used in a blood product device that centrifugally separates blood, and which transfers a separated predetermined blood component.

BACKGROUND ART

In recent technologies of blood transfusion, blood component transfusion is performed, in which components of blood (whole blood) obtained from blood donation and the like are separated, and only a component necessary for a patient is supplied. The blood component transfusion enables reduction of burdens or side effects on a patient's circulatory system and efficient use of the donated blood.

In the separation of the blood components, a centrifuge machine separates blood into a supernatant (platelet poor plasma) fraction, a heavy precipitation (concentrated red blood cell) fraction, and buffy coat formed therebetween. These components are transferred to predetermined preservation bags, using a blood bag system attachable to the centrifuge machine. The blood bag system disclosed in the specification of U.S. Pat. No. 6,910,998 includes a blood bag in which blood is preserved, a tube with one end connected to the blood bag, and a preservation bag to which the other end of the tube is connected. For example, a centrifugally separated supernatant liquid (supernatant fraction) is transferred to the preservation bag from the blood bag through the tube.

By the way, in the blood bag system attached to the centrifuge machine as described above, the blood is spread from the blood bag to the tube extending to the preservation bag, and a slight amount of the blood is transferred to the tube extending to the preservation bag, when the blood is preserved in the blood bag by blood donation or the like (or before centrifugal separation is performed). Such transferred blood does not especially influence on quality of a blood component even if the blood is mixed in a supernatant liquid circulated in the tube. However, the color of whole blood (red blood cells) stands out from the supernatant liquid. Therefore, even if a very small amount of blood is mixed, a user and the like may feel the quality of the blood product has low quality.

SUMMARY OF INVENTION

The present invention has been made in view of the foregoing, and an objective is to provide a blood bag system that can substantially suppress mixture of another component to a predetermined centrifuged blood component, thereby to obtain a high quality blood product, and to obtain a plasma product having less contamination of red blood cells.

To achieve the above objective, the present invention is a blood bag system including a blood bag to which centrifugal force is provided in a state where whole blood or a blood component is stored, and a tube that circulates a fluid centrifugally separated from the blood bag, wherein the tube includes an extending portion extending in an approximately perpendicular direction to a centrifugal direction into which the centrifugal force is applied, and a storage portion that can store the fluid existing in the extending portion is provided at a side of the centrifugal direction of the extending portion.

According to the above description, the blood bag system can move the fluid in the extending portion to the centrifugal direction by providing of centrifugal force, and can allow the fluid to flow in to the storage portion, by including the storage portion at the side of the centrifugal direction of the extending portion. Therefore, for example, even if blood exists in the extending portion of the tube that transfers plasma at the time of centrifugal separation, the blood subject to the centrifugal force can be favorably stored. As a result, inconvenience caused by the blood to the plasma can be substantially suppressed, and the plasma can be favorably transferred. Accordingly, the blood bag system can obtain a high quality blood product (plasma).

In this case, the storage portion is favorably a branch tube extending in the centrifugal direction.

The storage portion is the branch tube as described above, so that the branch tube acts along the centrifugal direction when the centrifugal force is provided. Therefore, the storage portion can smoothly store the fluid existing in the extending portion.

Further, the storage portion may have a configuration to be deformed to have a space in which the fluid can be stored by the application of the centrifugal force to the fluid.

The space of the storage portion is deformed by the application of the centrifugal force to the fluid as described above, so that the fluid can be easily stored in the space. Further, if the storage portion has the configuration to be deformed, an installation location of the storage portion on a cassette that holds the tube can be freely set.

Further, the extending portion and the storage portion are favorably integrally formed.

If the extending portion and the storage portion are integrally formed as described above, the fluid can be smoothly guided to the storage portion without being leaked to an outside.

Here, the blood bag and the tube may be attached to a cassette at the time of providing the centrifugal force, and may be held in a horizontal direction by the cassette.

The extending portion and the storage portion are held in the horizontal direction by the cassette as described above, so that when the centrifugal force is provided to the extending portion and the storage portion, movement of the fluid inside the tube can be favorably encouraged.

DESCRIPTION OF EMBODIMENTS

Hereinafter, favorable embodiments of a blood bag system according to the present invention will be provided and specifically described with reference to the appended drawings.

A blood bag system 10 according to the present embodiment is applicable to a blood product device 12 (centrifuge machine), and is configured to transfer and preserve respective components of blood (whole blood) centrifugally separated by the blood product device 12 into different bags. Specifically, the whole blood is separated by centrifugal separation into three components including plasma (supernatant liquid) that is a low specific gravity component, buffy coat that is an intermediate specific gravity component, and concentrated red blood cells (precipitation liquid). Further, the separated concentrated red blood cells are separated and preserved in a saline adenine glucose mannitol (SAG-M) liquid (hereinafter, referred to as RC-SAGM) that is a red blood cell preservation solution, and in a concentrated red blood cells (leukocyte reduced red cells concentrates, hereinafter, referred to as LR-RCC) obtained such that white blood cells are removed from the RC-SAGM.

Figure 1:
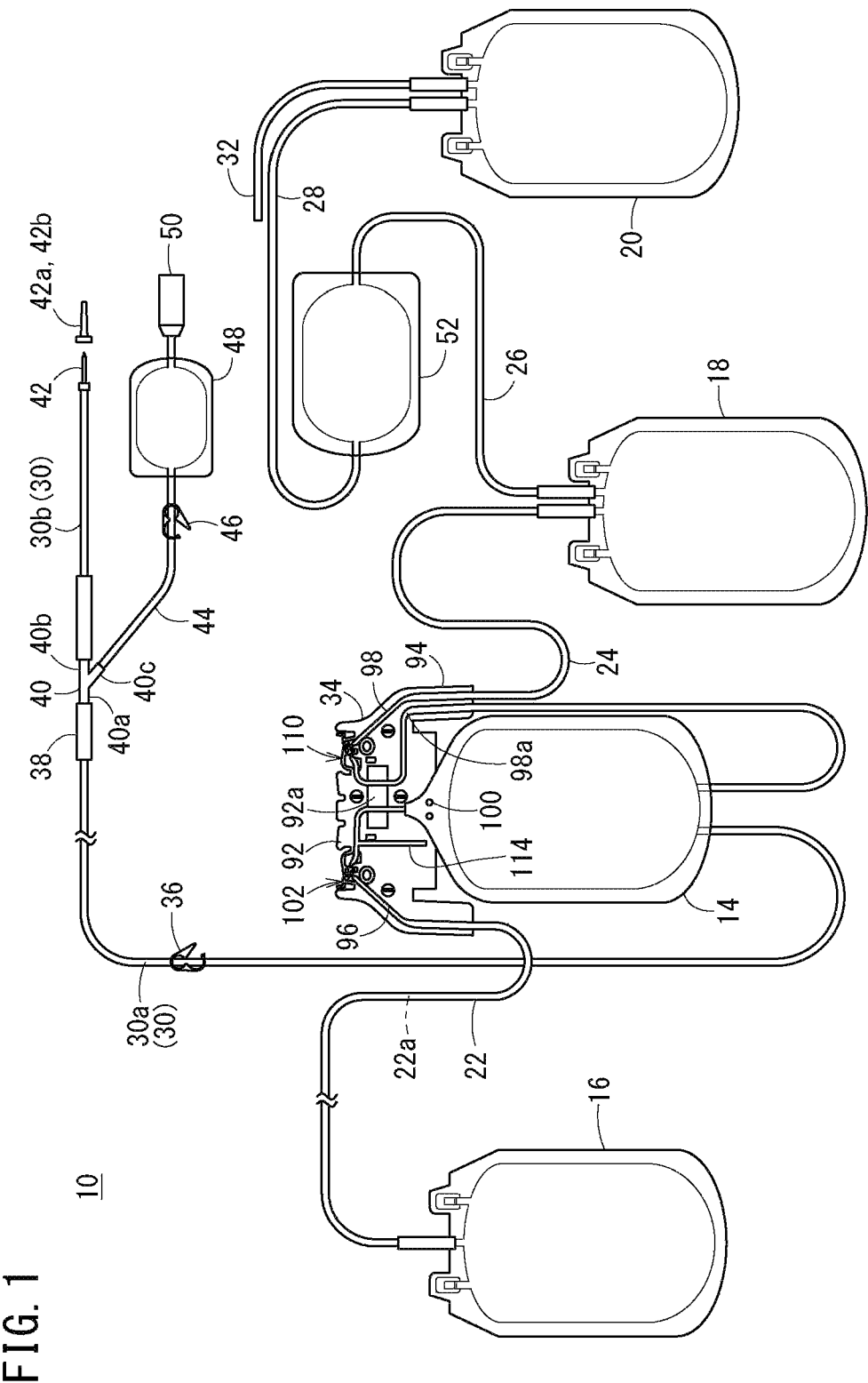
FIG. 1 is a schematic explanatory diagram illustrating an overall configuration of a blood bag system according to an embodiment of the present invention.

As illustrated in FIG. 1, the blood bag system 10 includes a blood bag 14, a plasma bag 16, an RC-SAGM bag 18, and an LR-RCC bag 20. The bags are connected by a plurality of tubes (first to fourth tubes 22, 24, 26, and 28) that can allow blood components to circulate therein.

The blood bag 14, the plasma bag 16, the RC-SAGM bag 18, and the LR-RCC bag 20 are formed into a bag shape such that sheet materials having flexibility are layered, and peripheral sealing portions of the layered sheet materials are bonded (through thermal fusion bonding or high-frequency fusion bonding) or glued. Examples of a material that configures the sheet materials include a material made of a flexible resin such as polyvinyl chloride or polyolefin.

Further, transparent and flexible resin tube is applied to the first to fourth tubes 22, 24, 26, and 28 (including a blood collecting tube 30 and a sample tube 32 described below). Clamps (not illustrated) are appropriately attached to intermediate positions of the first to fourth tubes 22, 24, 26, and 28, and can close and open flow paths of the first to fourth tubes 22, 24, 26, and 28 as needed. For example, the clamps are in an open state at the time of sterilization of the blood bag system 10 and at the time of preservation of the blood bag system 10 before use, so that insides of the bags are caused to communicate into each other and be in a uniform sterilization state.

The blood bag 14 (first bag) is a bag used for storing the whole blood or storing a separated blood component at the time of blood collection from a donor. Further, the blood bag 14 is also used to store and preserve the buffy coat that is a residual component of after the whole blood is centrifugally separated, and the plasma is transferred to the plasma bag 16 and the concentrated red blood cells are transferred to the RC-SAGM bag 18, as described below. That is, the blood bag 14 serves as both of a bag for storing the whole blood before separation and a bag for storing the buffy coat after separation.

A blood preservation solution having a blood anticoagulant property is favorably preserved in the blood bag 14. As the blood preservation solution, a blood preservation solution containing a citric acid, a phosphoric acid, and glucose (citrate phosphate dextrose (CPD)) can be favorably used.

The blood bag 14 is attached to a cassette 34 that can hang and support the blood bag 14. The cassette 34 is formed into a wide-width planar shape and a flat box shape having a predetermined thickness, and is mounted to an insert unit 60 of a blood product device 12 described below. Note that FIG. 1 illustrates a state in which one surface of the cassette 34 faces the same direction of the blood bag 14. In the centrifugal separation, the cassette 34 is horizontally tilted to the hung blood bag 14, and is attached to the insert unit 60.

One end of the first tube 22 is connected to an upper portion of the blood bag 14, and one end of the second tube 24 and one end of the blood collecting tube 30 are connected to a lower portion of the blood bag 14.

The first tube 22 is a tube for transferring the plasma that is the low specific gravity component. The first tube 22 goes above the blood bag 14, and a part of the first tube 22 is fixed and held to a planar portion of the cassette 34. Further, the first tube 22 extends from a predetermined position of the cassette 34 in a free state, and the other end portion of the first tube 22 is connected to the plasma bag 16.

The second tube 24 is a tube for transferring the concentrated red blood cells, and one end portion of the second tube 24 is connected to a lower portion of the blood bag 14, so that the second tube 24 can send the concentrated red blood cells that are the centrifugally separated high specific gravity components. Further, the second tube 24 also goes from the lower portion of the blood bag 14 to above the blood bag 14, so that a part of the second tube 24 is fixed and held to the planar portion of the cassette 34. The second tube 24 extends from an opposite position of the first tube 22 in a free state and is connected to the RC-SAGM bag 18.

Meanwhile, the blood collecting tube 30 is a tube used to preserve the whole blood of a donor to the blood bag 14 at the time of blood collection. A clamp 36 that closes and opens a flow path of the blood collecting tube 30 is provided in an intermediate portion of the blood collecting tube 30 (base end-side blood collecting tube 30a). One end of a sealing member 38 (breaking communication member or frangible barrier) is connected to one end of the base end-side blood collecting tube 30a. The sealing member 38 is configured such that a flow path is closed in an initial state and is opened with a breaking operation.

A first port 40a of the three-port connector 40 is connected to the other end of the sealing member 38. One end of the blood collecting tube 30 (tip-side blood collecting tube 30b) is connected to a second port 40b of the three-port connector 40, and a blood collecting needle 42 is connected to the other end of the tip-side blood collecting tube 30b. A cap 42a is mounted to the blood collecting needle 42 before use, and a needle guard 42b is mounted to the blood collecting needle 42 after use.

One end of a branch blood collecting tube 44 is connected to a third port 40c of the three-port connector 40. A clamp 46 that closes and opens a flow path of the branch blood collecting tube 44 is provided in an intermediate portion of the branch blood collecting tube 44. A sample blood bag 48 is connected to the other end of the branch blood collecting tube 44. When the whole blood is collected from the donor, first, a predetermined amount of an initial flow (collected blood initial flow) of the collected whole blood is stored in the sample blood bag 48 before the whole blood is stored in the blood bag 14. In this case, when the clamp 46 is caused to be in an open state while the sealing member 38 is kept in a close state (initial state), an inflow of the collected blood initial flow to the base end-side blood collecting tube 30*a* side, that is, to the blood bag 14 side is prevented. Then, the collected blood initial flow can be introduced to the sample blood bag 48 through the blood collecting tube 30, the three-port connector 40, and the branch blood collecting tube 44.

A sampling port 50 is connected to the sample blood bag 48, and a blood sampling tube (not illustrated) is mounted to the sampling port 50, so that the collected initial blood is collected in the blood sampling tube. The collected initial blood is used as blood for examination. Note that the features from the three-port connector 40 to the sampling port 50 may be omitted depending on a use.

Meanwhile, the first tube 22 is connected to an upper portion of the plasma bag 16 (second bag), so that the plasma bag 16 stores and preserves the plasma transferred from the blood bag 14.

The second tube 24 is connected to an upper portion of the RC-SAGM bag 18 (third bag), so that the RC-SAGM bag 18 stores and preserves the concentrated red blood cells transferred from the blood bag 14. The SAGM that is a mixture solution containing mannitol, glucose, adenine, and sodium chloride is preserved in the RC-SAGM bag 18, as the blood preservation solution having an anticoagulant property of the concentrated red blood cells, as described above.

The LR-RCC bag 20 (fourth bag) is a bag for storing and preserving the LR-RCC, and is connected to the RC-SAGM bag 18 through the third and fourth tubes 26 and 28. A filter 52 that can remove white blood cells (predetermined components) is provided between the third tube 26 and the fourth tube 28, and the concentrated red blood cells (LR-RCC) from which the white blood cells have been removed are allowed to flow into an inside of the LR-RCC bag 20 through the filter 52. The sample tube 32 that can take out a part of the LR-RCC is connected to an upper portion of the LR-RCC bag 20, in addition to the fourth tube 28. That is, the blood bag system 10 can confirm a state of the LR-RCC.

Figure 2:
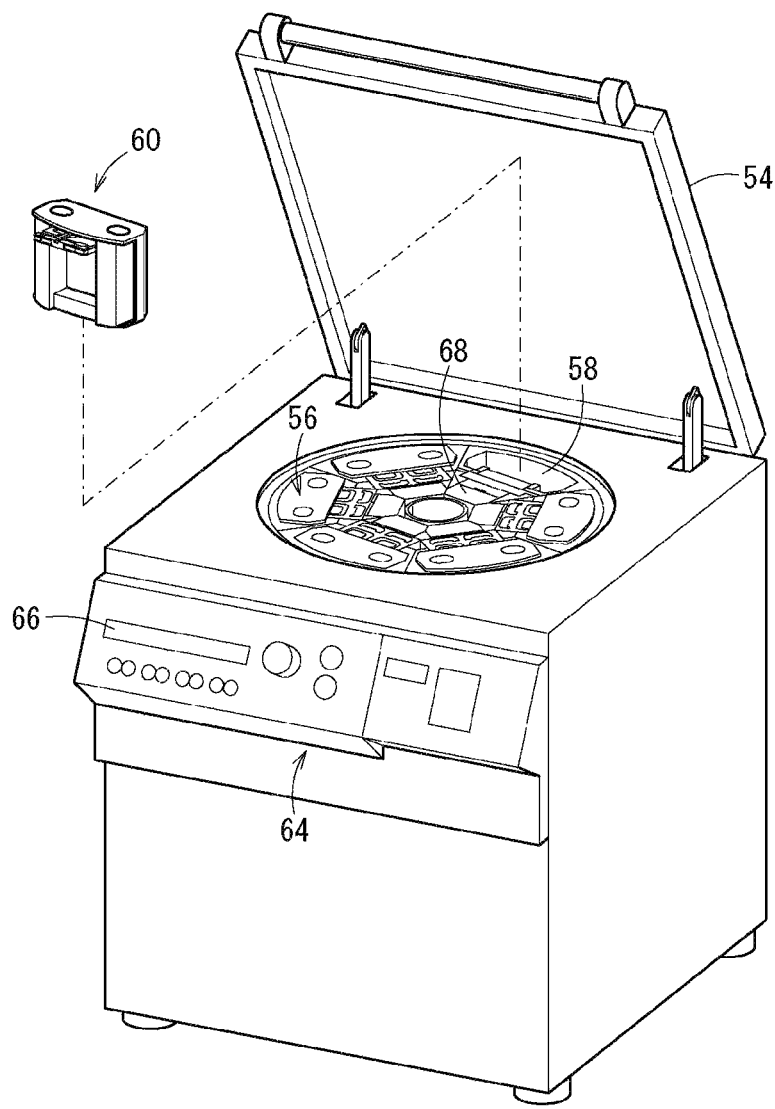
FIG. 2 is a perspective view of a blood product device that stores the blood bag system of FIG. 1.

The blood bag system 10 according to the present embodiment is applied to the blood product device 12 as illustrated in FIG. 2, for example. The blood product device 12 is used to centrifugally separate the whole blood stored in the blood bag 14 into the three layers of the plasma, the buffy coat, and the concentrated red blood cells, to transfer the plasma to the plasma bag 16, and to transfer the concentrated red blood cells to the RC-SAGM bag 18.

Figure 3:
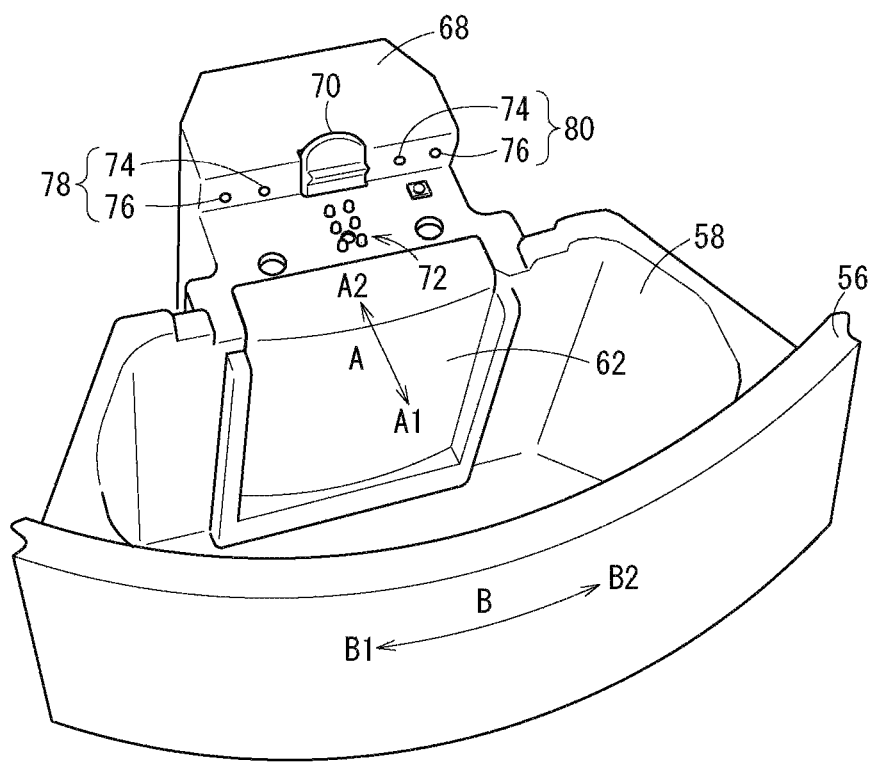
FIG. 3 is a perspective view illustrating a part of a centrifugal drum of the blood product device of FIG. 2.

To make understanding of a method of using the blood bag system 10 easy, a configuration of the blood product device 12 will be hereinafter described. Note that, in the description below, an arrow A direction in FIG. 3 is a radial direction, and an arrow B direction is a circumferential direction. In a precise sense, the circumferential direction is a direction along an arc like the arrow B. However, for convenience of description, a direction perpendicular to the arrow A in a described portion is also called the circumferential direction.

As illustrated in FIG. 2, the blood product device 12 has a box shape, and includes an openable/closable top surface cover 54, an internal centrifugal drum 56 (centrifugal separation means), six unit insertion holes 58 provided at equal angles (60°) in the centrifugal drum 56, six insert units 60 to be inserted to the respective unit insertion holes 58, and six plungers 62 (pressing means: see FIG. 3) provided in a central portion and advanceable/retractable to/from the respective insert units 60. The blood product device 12 is operated based on an operation of an operation unit 64 provided in front and is controlled by a microcomputer (not illustrated), and displays predetermined information on a monitor 66.

As illustrated in FIG. 3, the centrifugal drum 56 includes six-divided units along the circumferential direction, and is configured to be rotated at a predetermined speed. The whole blood stored in the blood bag 14 is separated by being provided centrifugal force according to the rotation of the centrifugal drum 56. In one unit, a central body 68 and a unit insertion hole 58 are integrally formed.

The central body 68 is provided with a holding lever 70, an electrode 72, a first rod 74, a second rod 76, and the plunger 62. The holding lever 70 is energized by an elastic body (not illustrated), and holds an end portion of the cassette 34.

The electrode 72 is electrically connected with a detection sensor (not illustrated) provided in a pedestal 90 (see FIG. 4) of the insert unit 60 when the insert unit 60 is inserted to the unit insertion hole 58. The detection sensor individually detects the plasma circulating in the first tube 22 and the concentrated red blood cells circulating in the second tube 24, and transmits detection signals to the blood product device 12. The blood product device 12 can discriminate a circulation state (timing of circulation start, circulation termination, and the like) of the centrifugally separated blood components, based on the detection signals.

The first and second rods 74 and 76 are selectively advanceable/retractable in the radial direction A. The first and second rods 74 and 76 on a first side in circumferential direction B1 comprise first clamp drive means 78 that performs open/close operations of a first clamp mechanism 102 (see FIG. 4) of the cassette 34. The first and second rods 74 and 76 on a second side in circumferential direction B2 comprise second clamp drive means 80 that perform open/close operations of a second clamp mechanism 110 (see FIG. 4).

The plunger 62 has a function to press the blood bag 14 during the centrifugal separation, by being provided in an inner wall of the unit insertion hole 58 and selectively advanceable/retractable in a radially inward A2. The plasma and the concentrated red blood cells separated in the blood bag 14 are allowed to flow out from the blood bag 14 by providing of the pressing force.

Figure 4:
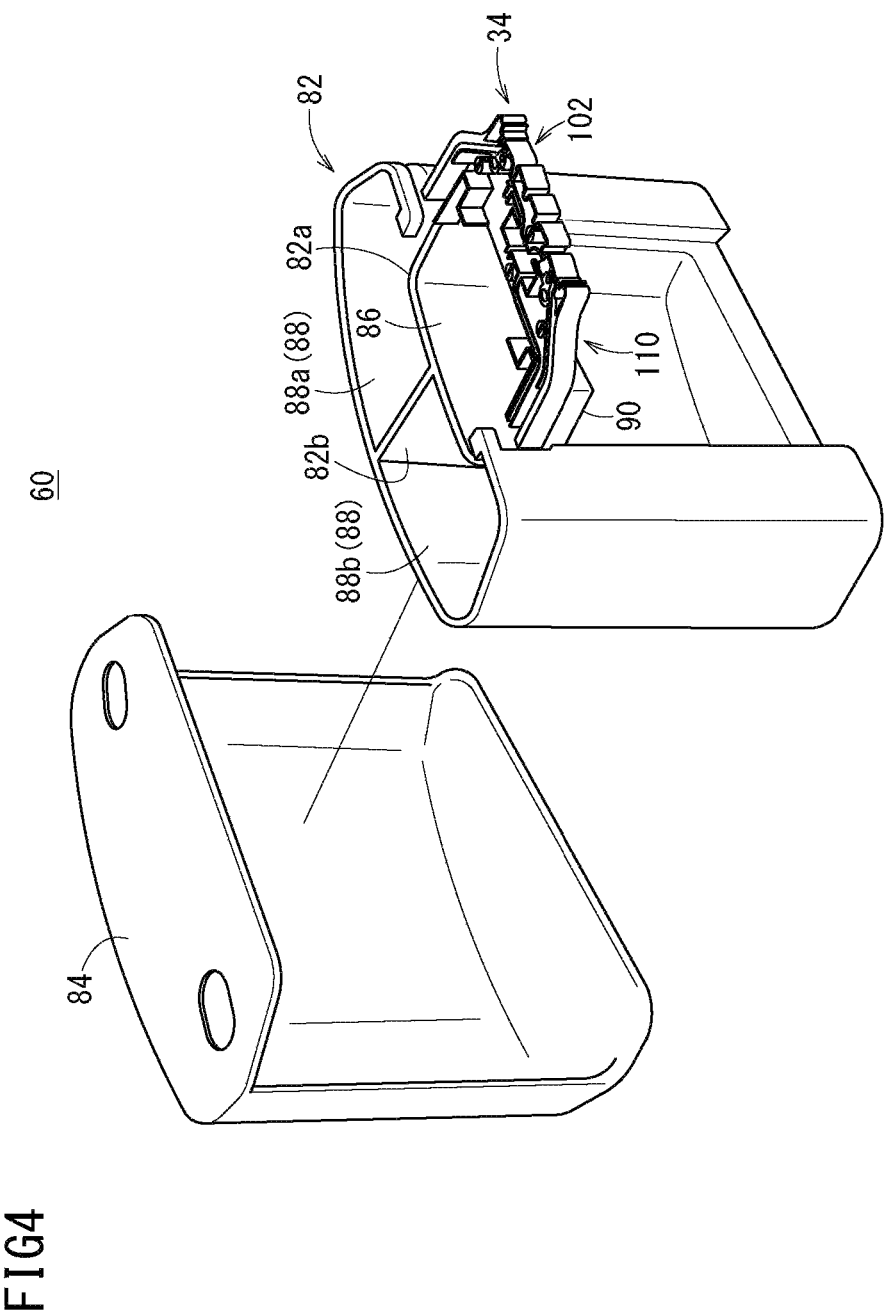
FIG. 4 is a partially exploded perspective view illustrating an insert unit of FIG. 2.

As illustrated in FIG. 4, the insert unit 60 includes a unit main body 82 and a cover body 84. The unit main body 82 is a cylinder with a bottom surface and an upper opening, exhibiting a wide-width arc shape in a plan view. The unit main body 82 includes a radially inward small chamber 86 (hereinafter, referred to as first chamber 86) and an radially outward large chamber 88, by partitioning an inside of the cylinder with an arc-shaped wall 82*a*. Not only the upper opening but also a radially inward side of the first chamber 86 is open. The pedestal 90 protruding in the radially inward direction A2 is provided on a radially inward upper portion of the first chamber 86, and the cassette 34 is attached to an upper surface of the pedestal 90. Further, the large chamber 88 is divided into a second chamber 88*a* at the first circumferential direction B1 side and a third chamber 88*b* at the second circumferential direction B2 side across a wall 82*b* provided in an approximately central portion of the circumferential direction B.

The cassette 34 includes a cassette main body 92 that fixes and holds the tubes, and a cover (not illustrated) attached to an upper surface of the cassette main body 92. The cassette main body 92 is formed such that a radially outward direction A1 side becomes wide in width and the radially inward direction A2 side becomes narrow in width, corresponding to the central body 68 of the centrifugal drum 56 in a plan view (see FIG. 1). A pair of extension portions 94 protruding in the radially outward direction A1 by a predetermined length is provided at both sides of the circumferential direction B, of the cassette main body 92. Further, an opening portion 92*a* extending in the circumferential direction B is provided in a central portion of the cassette main body 92, and the above-described detection sensor is inserted in the opening portion 92*a*.

A first guide flow path 96 for guiding the first tube 22, a second guide flow path 98 for guiding the second tube 24, and two pins 100 for supporting the blood bag 14 are provided on the upper surface of the cassette main body 92. The first and second guide flow paths 96 and 98 are built such that walls that can hold the first and second tubes 22 and 24 are provided in a plurality of places.

Figure 5:
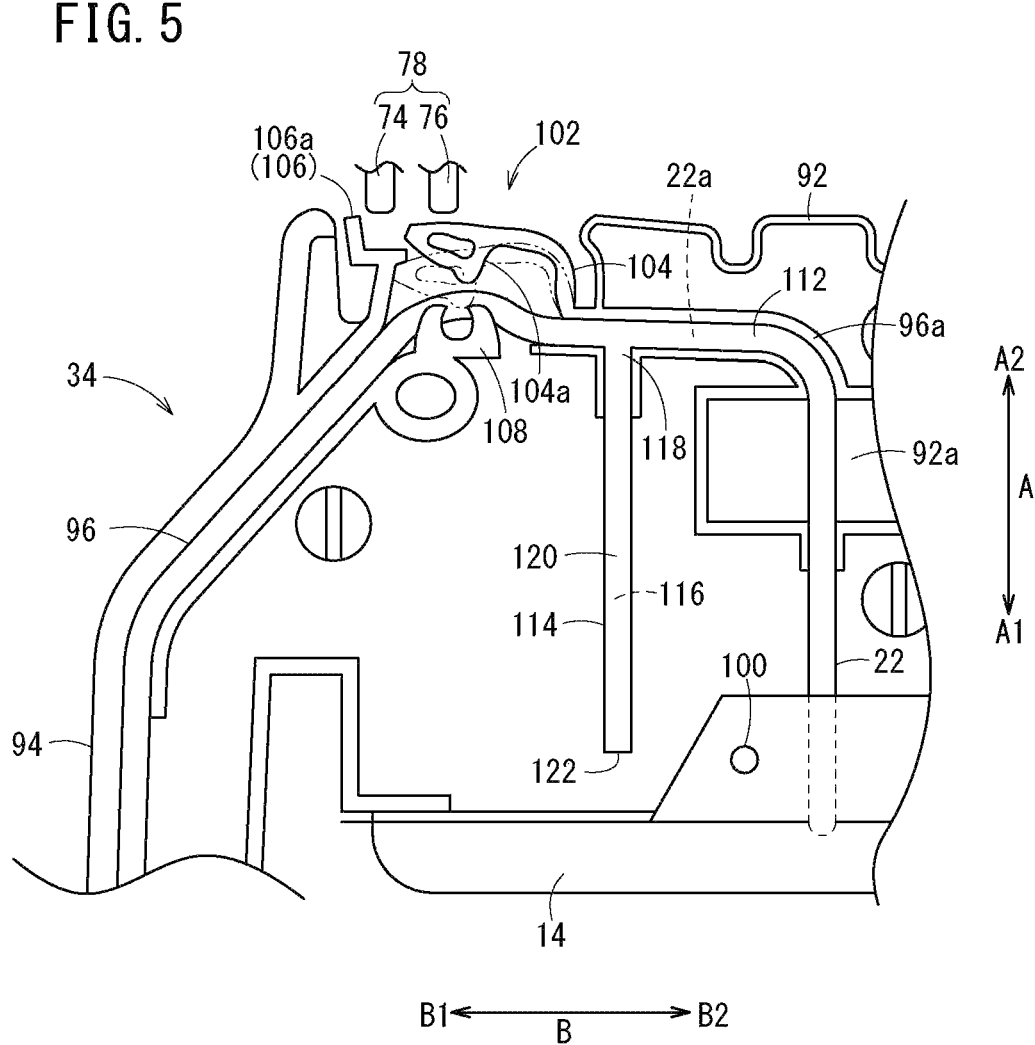
FIG. 5 is a plan view illustrating an attaching relationship between a cassette and a first tube of FIG. 1.

As illustrated in FIGS. 1 and 5, the first guide flow path 96 goes from around the center of an end portion of the radially outward direction A1, of the cassette 34, toward the radially inward direction A2, is bent at an intermediate portion in the first circumferential direction B1, and extends from a bent portion 96*a* to a side surface of the first circumferential direction B1, of the cassette 34. Further, the first guide flow path 96 extends toward the radially outward direction A1 along the side surface of the first circumferential direction B1, and reaches an end portion of the radially outward direction A1, of the extension portion 94 of the first circumferential direction B1. In a middle of the first guide flow path 96 where a groove in the circumferential direction B is formed, there is a first clamp mechanism 102 for blocking and opening a flow path 22*a* of the first tube 22.

The first clamp mechanism 102 includes a block piece portion 104 elastically displaceable in the radial direction A, an engaging piece portion 106 that can engage the block piece portion 104, and a tube support portion 108 facing the block piece portion 104. An approximately triangular contact portion 104*a* is formed in a tip side of the block piece portion 104, and is pressed by the first rod 74, thereby to be displaced in the radially outward direction A1 side. Accordingly, the contact portion 104*a* squashes the first tube 22 in cooperation with the tube support portion 108, and can block the flow path 22*a* of the first tube 22.

The engaging piece portion 106 engages a tip end of the contact portion 104*a*, with the displacement of the block piece portion 104 in the radially outward direction A1. Accordingly, the first clamp mechanism 102 prevents elastic return of the block piece portion 104 to the radially inward direction A2 side, and continues blockage of the flow path 22*a* of the first tube 22. In the first clamp mechanism 102, a recessed portion 106*a* of the engaging piece portion 106 is pressed by the second rod 76, thereby being displaced in the first circumferential direction B1, and releasing engagement of the block piece portion 104 (that is, opening the flow path 22*a* of the first tube 22).

Meanwhile, as illustrated in FIG. 1, the second guide flow path 98 goes from an end portion of the radially outward direction A1, of the extension portion 94 of the second circumferential direction B2 of the cassette 34 toward the radially inward direction A2, is bent in an intermediate portion, and extends in the first circumferential direction B1. Further, the second guide flow path 98 is bent again at a position extending from a bent portion 98*a* to the first circumferential direction B1 by a predetermined length (the position passes through the opening portion 92*a*) toward the radially inward direction A2, and is then formed to trace a passage approximately symmetrical to the first guide flow path 96. That is, the second guide flow path 98 loops around a right half of the cassette main body 92 from the end portion of the radially outward direction A1, of the extension portion 94 of the second circumferential direction B2, and reaches the same end portion of the radially outward direction A1, of the same extension portion 94.

The second clamp mechanism 110 for blocking and opening the flow path of the second tube 24 is provided in a middle of the second guide flow path 98 where a groove in the circumferential direction B is formed (a symmetrical position to the first clamp mechanism 102). The second clamp mechanism 110 is formed in a symmetrical shape to the first clamp mechanism 102.

Referring back to FIG. 4, the cover body 84 is mounted to the unit main body 82 from an outer side. The cover body 84 reliably holds the blood bag system 10 mounted to the unit main body 82, by covering the outer side surface, the upper surface, and the lower surface of the unit main body 82.

The insert unit 60 configured as described above is inserted and mounted to the centrifugal drum 56 (unit insertion hole 58) (see FIG. 2), so that the centrifugal separation of the whole blood is performed by the blood product device 12. At this time, the blood bag system 10 is attached to the insert unit 60 in a state where the respective bags and tubes are connected (in a built state of the system).

Specifically, the blood bag 14 in which the whole blood collected from the donor is stored is attached to the cassette 34, and is accommodated in the first chamber 86 of the unit main body 82. The cassette 34 becomes horizontal (tilted by 90°) to the blood bag 14 by being placed on the pedestal 90 and attached to the unit main body 82. Further, other bags (the plasma bag 16, the RC-SAGM bag 18, and the LR-RCC bag 20) are accommodated in the large chamber 88 of the unit main body 82 in a state where the first to fourth tubes 22, 24, 26, and 28 connect the respective bags, as illustrated in FIG. 1. Specifically, the plasma bag 16 is accommodated in the second chamber 88*a*, and the RC-SAGM bag 18 and the LR-RCC bag 20 are accommodated in the third chamber 88*b*. Note that the blood collecting tube 30 is blocked and sealed at a predetermined position (a position close to the blood bag 14) at the time of centrifugal separation.

Here, the first tube 22 is held by the first guide flow path 96 on the upper surface of the cassette 34, and the second tube 24 is held by the second guide flow path 98. Therefore, as illustrated in FIG. 5, the first tube 22 is installed to exhibit the extending portion 112 extending toward the first circumferential direction B1, on the first guide flow path 96. That is, the extending portion 112 corresponds to a range from the bent portion 96*a* on the first guide flow path 96 to the first clamp mechanism 102. Since the cassette 34 is horizontally attached to the insert unit 60, the extending portion 112 horizontally extends on a plane (on the same height) of the cassette 34, and is fixed perpendicularly to the radial direction A of the centrifugal drum 56. Therefore, the extending portion 112 is perpendicular to the direction (centrifugal direction) into which the centrifugal force is applied from the centrifugal drum 56.

Here, in the blood bag system 10 configured as described above, there is a possibility that the whole blood is moved to the first tube 22 (extending portion 112) when the whole blood is stored in the blood bag 14 (or after the whole blood is stored), as described above. That is, in the blood bag system 10, while the first tube 22 is closed and the blood is collected in the first clamp mechanism 102, the whole blood flows through the flow path 22a of the first tube 22 up to the first clamp mechanism 102, by being diluted by an anticoagulant agent moved to the first tube 22. The extending portion 112 is perpendicular to the centrifugal direction in the state where the whole blood exists in the extending portion 112. Therefore, even if the centrifugal force is provided at the time of a centrifugation step, the whole blood remains in the extending portion 112 without being returned to the blood bag 14. Then, when the plasma is pushed and circulates in the first tube 22 at the time of a transfer step after the centrifugation step, the whole blood is mixed with the supernatant liquid (plasma) and transferred to the plasma bag 16 (especially, an inconvenience of inflow of the red blood cells to the plasma bag 16 becomes a problem. Therefore, hereinafter, a residue in the extending portion 112 is referred to as red blood cell contamination C).

In the blood bag system 10 according to the present embodiment, the branch tube 114 (storage portion) is provided to the extending portion 112 of the first tube 22 in order to store the red blood cell contamination C at the time of centrifugal separation. That is, the branch tube 114 has a function to prevent the red blood cell contamination C from flowing into the plasma bag 16, by storing the red blood cell contamination C.

This branch tube 114 is formed to be perpendicular to the extending portion 112, and extends in the centrifugal direction (radially outward direction A1). The branch tube 114 is integrally formed to the extending portion 112 (that is, to the first tube 22), and has a storage space 116 having an internal diameter similar to the extending portion 112. The entire length of the branch tube 114 is formed such that the storage space 116 has an enough volume to store the red blood cell contamination C.

The branch tube 114 includes a connection end 118 connected to the extending portion 112, a body portion 120 continuing to the connection end 118, and an extension end 122 that is an opposite-side end portion to the connection end 118, and continues to the body portion 120. A peripheral portion of the connection end 118 is fixed and held by a wall that configures the first guide flow path 96. Accordingly, an angle of the branch tube 114 to the extending portion 112 can be easily kept to a perpendicular direction (90°). Meanwhile, the extension end 122 is not especially fixed and held, and is in a free state by the body portion 120 extending from the connection end 118. As described above, the branch tube 114 has the radially outward direction A1 side of the connection end 118 being in the free state, thereby to easily cause the extension end 122 to be along the centrifugal direction, when the centrifugal force is provided.

Further, the branch tube 114 is favorably provided in a position near the first clamp mechanism 102. Accordingly, the branch tube 114 can reliably move the red blood cell contamination C approaching in the vicinity of the first clamp mechanism 102 to the storage space 116.

Further, the extension end 122 of the branch tube 114 favorably has a configuration to prevent outflow of the fluid and to easily allow the air to be released. Accordingly, the air can be released at the time of centrifugal separation, and transfer of the red blood cell contamination C in the storage space 116 can be easily encouraged.

The blood bag system 10 according to the present embodiment is basically configured as described above. Hereinafter, functions and effects of the blood bag system 10 will be described based on a procedure of generating a blood product.

First, FIG. 1 is referred. The blood bag system 10 is brought to be in a state where the respective bags and tubes are connected before blood collection of a donor, the blood bag 14 is attached to the cassette 34, and the first and second tubes 22 and 24 are installed.

When the blood is collected from the donor, first, the collected blood sample is collected in the sample blood bag 48, as described above. After the collected blood initial flow is collected, the clamp 46 closes the branch tube 114, and the above-described breaking operation is performed on the sealing member 38, so that the flow path of the blood collecting tube 30 is opened. At this time, the clamp 36 causes the blood collecting tube 30 to be in the open state, and the first and second clamp mechanisms 102 and 110 of the cassette 34 cause the flow paths of the first and second tubes 22 and 24 to be in the close state. Then, the blood (whole blood) of the donor flows into the blood bag 14 through the blood collecting tube 30. When a predetermined amount of blood has been collected and stored in the blood bag 14, the blood collecting tube 30 is bonded and sealed with a tube sealer or the like, and then the blood collecting tube 30 is blocked at the sealed portion.

Next, the blood bag system 10 in a state where the blood collecting tube 30 is blocked is mounted to the insert unit 60. At this time, the plasma bag 16 and the RC-SAGM bag 18 are favorably accommodated in the large chamber 88 of the insert unit 60 (the plasma bag 16 is accommodated in the second chamber 88a and the RC-SAGM bag 18 is accommodated in the third chamber 88b) in an unbent state so that the plasma and the concentrated red blood cells can smoothly flow in and be stored, in the transfer step after the centrifugation step. The filter 52 and the LR-RCC bag 20 are not used in the centrifugation step and the subsequent transfer step, and thus are accommodated in the large chamber 88 after being made compact by being folded or bent. Accordingly, the storage space for the plasma bag 16 and the RC-SAGM bag 18 can be secured. When the blood bag system 10 is mounted and accommodated in the unit main body 82, the cover body 84 is mounted to the unit main body 82, so that the insert unit 60 is caused to be in an assembled state.

Next, as illustrated in FIG. 2, the insert unit 60 to which the blood bag system 10 is mounted is inserted to the unit insertion hole 58 of the blood product device 12. Accordingly, the holding lever 70 fixes an end portion of the cassette 34. Further, the detection sensor or a contact point of an interface circuit of the insert unit 60 is electrically connected to the electrode 72. Basically, the six insert units 60 are mounted to the blood product device 12. However, five or less insert units 60 (favorably, three or two insert units 60 at equal angles) may be mounted as long as the insert units 60 can be well balanced.

Figure 6A:
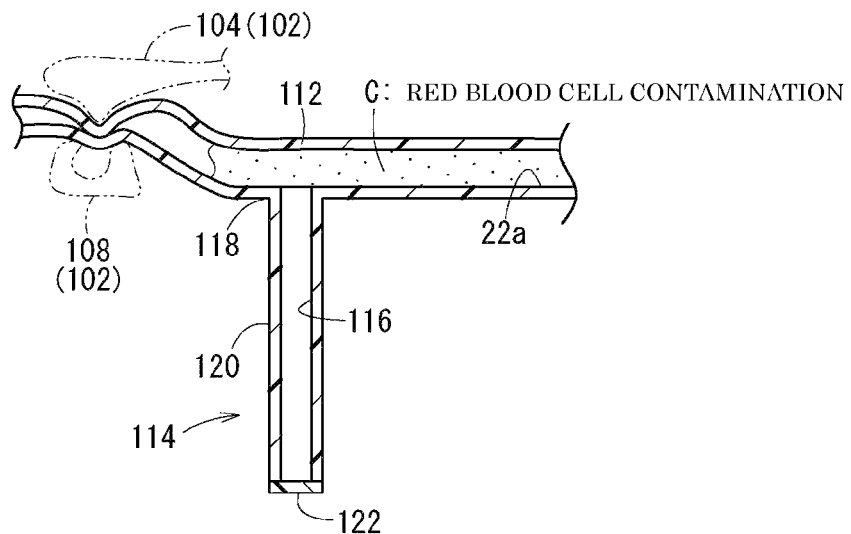
FIG. 6A is a first plan sectional view for describing a function of a branch tube of FIG. 5.
Figure 6B:
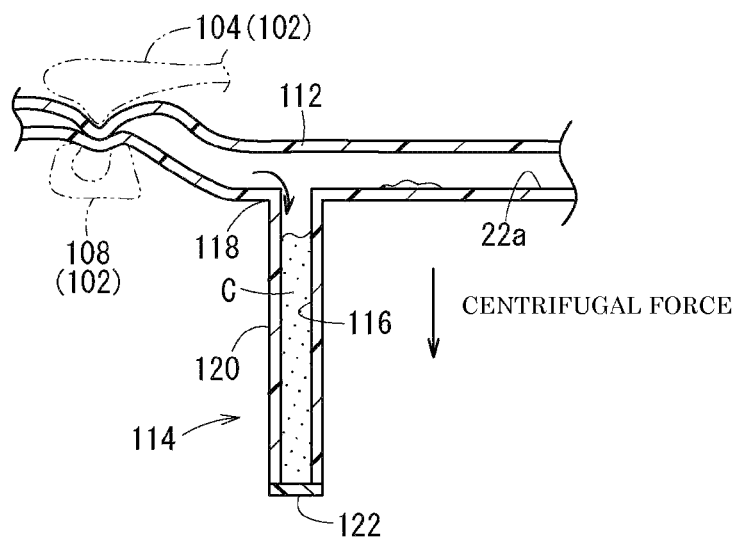
FIG. 6B is a second plan sectional view continuing to FIG. 6A.
Figure 6C:
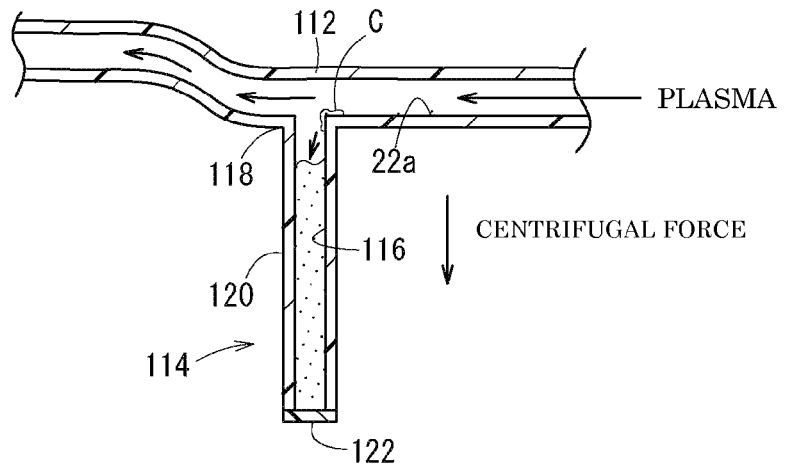
FIG. 6C is a third plan sectional view continuing to FIG. 6B.

Here, at the time of blood collecting or attachment to the insert unit 60, there is a possibility that the whole blood (red blood cell contamination C) stored in the blood bag 14 is moved to the flow path 22a of the first tube 22, as described above. While the movement of the red blood cell contamination C is stopped at the closed portion of the first tube 22 with the first clamp mechanism 102, the whole blood remains inside the flow path 22a of the extending portion 112, as illustrated in FIG. 6A. Note that a state where a large amount of the red blood cell contamination C exists in the extending portion 112 is illustrated in FIGS. 6A to 6C for easy understanding. However, in reality, a small amount of the red blood cell contamination C exists in the extending portion 112.

In generation of a blood product, after the cover 54 is closed, the centrifugation step and the transfer step are automatically performed by operation of the operation unit 64.

Figure 7:
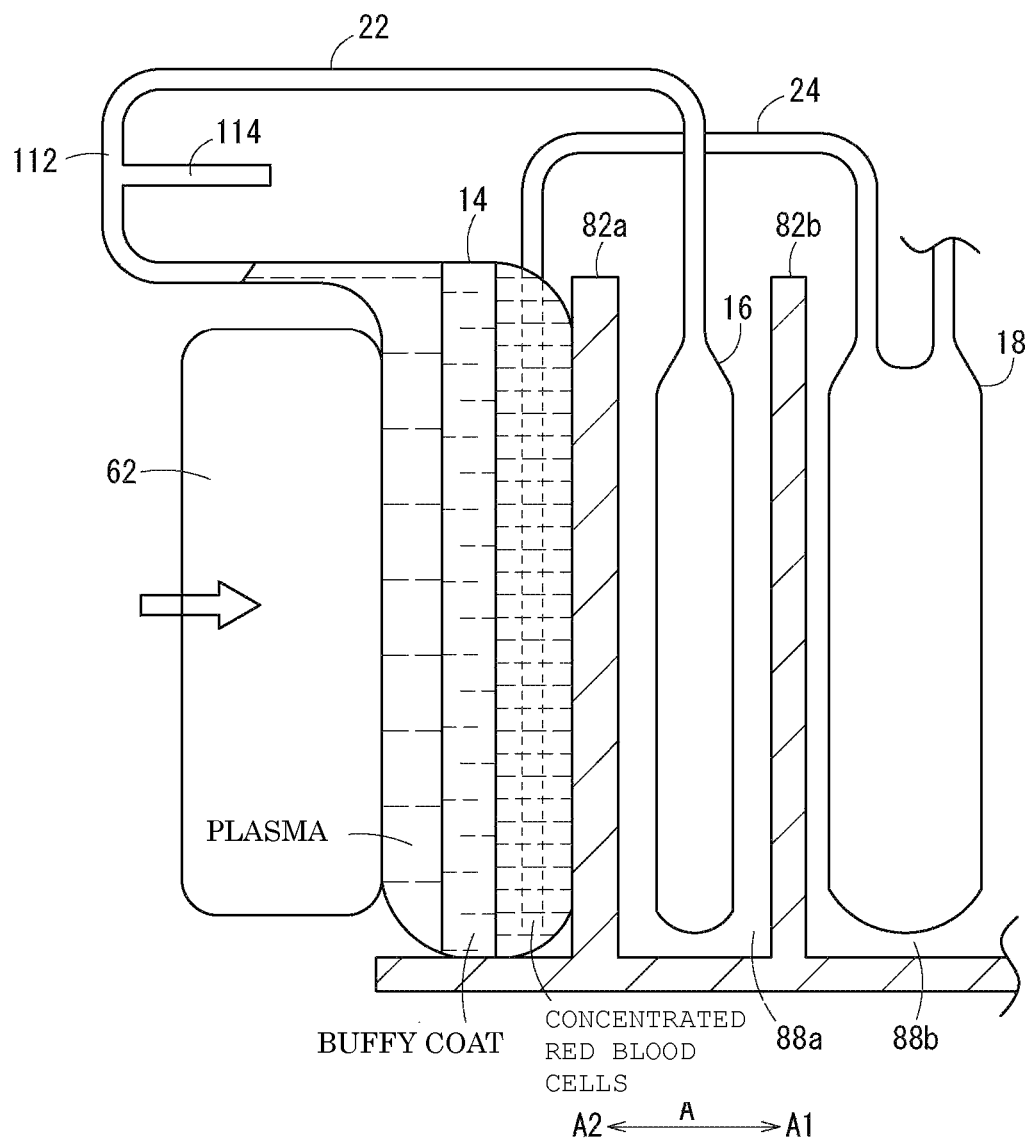
FIG. 7 is a schematic diagram for describing a function of the blood product device of FIG. 2.

In an automatic operation of the blood product device 12, first, the centrifugal step is performed by rotation of the centrifugal drum 56. At this time, the first and second clamp mechanisms 102 and 110 are closed in advance. However, the first rod 74 is driven and advanced to press the block piece portion 104 to ensure reliability. As illustrated in FIG. 7, in the centrifugation step, the whole blood stored in the blood bag 14 is subject to the centrifugal force, so that the concentrated red blood cells as the high specific gravity components are moved in the radially outward direction, the plasma as the low specific gravity component is moved in the radially inward direction, and the buffy coat as the intermediate specific gravity component is moved therebetween, to be separated into the three layers.

Then, in the centrifugation step, the red blood cell contamination C existing in the extending portion 112 is subject to the centrifugal force, and is moved to get close to the radially outward direction A1 side of the flow path 22a of the extending portion 112. As a result, as illustrated in FIG. 6B, the red blood cell contamination C flows into the branch tube 114 from the extending portion 112, and the inflow red blood cell contamination C is moved to the extension end 122 of the branch tube 114 along the centrifugal direction.

Especially, the branch tube 114 is provided in a position near the first clamp mechanism 102, and can smoothly guide the red blood cell contamination C in the extending portion 112 tilted in the centrifugal direction. Therefore, by performing of the centrifugation step, the red blood cell contamination C existing in the flow path 22a of the extending portion 112 is substantially decreased. Note that the red blood cell contamination C exists in the flow path 22a at an upstream side of the extending portion 112 (bent portion 96a) of the first tube 22. The red blood cell contamination C existing in this portion is moved to the blood bag 14 by providing of the centrifugal force.

The blood product device 12 is moved onto the transfer step after the centrifugation step. In the transfer step, the first and second clamp mechanisms 102 and 110 are operated while the rotation of the centrifugal drum 56 is maintained, so that the flow paths of the first and second tubes 22 and 24 are caused to be in the open state.

Next, as illustrated in FIG. 7, the plunger 62 is displaced in the radially outward direction A1 to press the blood bag 14. The blood bag 14 decreases the volume by being sandwiched by the plunger 62 and the wall. Therefore, the plasma flows out to the first tube 22 and the concentrated red blood cells flow out to the second tube 24. At this time, since the first tube 22 directs to the radially inward side, the plasma positioned closest to the radially inward side can be favorably caused to flow out from the blood bag 14. Further, since the second tube 24 directs to the radially outward side, the concentrated red blood cells positioned closest to the radially outward side can be favorably caused to flow out form the blood bag 14.

In the transfer step, as illustrated in FIG. 6C, the plasma is moved from the blood bag 14 to the extending portion 112 of the first tube 22. At this time, in the centrifugation step, because the red blood cell contamination C has been moved to the branch tube 114, the red blood cell contamination C does not remain in the extending portion 112, and the plasma can be moved in the first tube 22 without being mixed with the red blood cell contamination C. As a result, highly pure plasma is stored in the plasma bag 16.

Further, even if a small amount of the red blood cell contamination C remains in the extending portion 112, the centrifugal force is continuously applied at the time of the transfer step, so that the red blood cell contamination C is moved in the radially outward direction A1. Therefore, at an initial time of the transfer step, the remaining red blood cell contamination C is pushed to flow by the plasma, and can be moved from the extending portion 112 to the branch tube 114.

After the plasma and the concentrated red blood cells flow out from the blood bag 14, change of colors (concentration) of the first and second tubes 22 and 24 is detected by the detection sensor, and the flow paths of the first and second tubes 22 and 24 are closed by the first and second clamp mechanisms 102 and 110. Closing of the first tube 22 and the second tube 24 is separately performed, and when transfer of one blood component is not completed even if the other flow path is closed, advancing of the plunger 62 is continued and transfer of the one blood component is performed. As described above, by the separate closing of the first and second tubes 22 and 24, the plasma can accurately flow into the plasma bag 16, and the concentrated red blood cells can accurately flow into the RC-SAGM bag 18. Further, the buffy coat can favorably remain in the blood bag 14.

When the above-described transfer step is terminated, the blood bag system 10 is taken out from the insert unit 60. Further, the first tube 22 and the second tube 24 in the blood bag system 10 are cut after the first tube 22 and the second tube 24 are bonded and sealed, and the bags are separated. As a result, the plasma is stored in the plasma bag 16, the buffy coat is stored in the blood bag 14, and the concentrated red blood cells are stored in the RC-SAGM bag 18. Note that a part of the concentrated red blood cells stored in the RC-SAGM bag 18 is transferred to the LR-RCC bag 20 through the third tube 26, the filter 52, and the fourth tube 28. At this time, the white blood cells are removed in the filter 52, so that the LR-RCC is favorably stored in the LR-RCC bag 20.

As described above, according to the blood bag system 10 of the present embodiment, the branch tube 114 (storage portion) is provided at the centrifugal direction side of the extending portion 112, so that the red blood cell contamination C in the extending portion 112 is moved in the centrifugal direction when the centrifugal force is applied. That is, the branch tube 114 can favorably store the red blood cell contamination C. Therefore, the first tube 22 can substantially suppress mixture of the red blood cell contamination C to the transferred plasma, and can favorably transfer the plasma. Accordingly, the blood bag system 10 can obtain a high quality blood product (plasma).

In this case, the storage portion of the red blood cell contamination C is formed in the branch tube 114 branching from the extending portion 112, so that the branch tube 114 acts along the centrifugal direction when the centrifugal force is applied. Therefore, the branch tube 114 can smoothly house the red blood cell contamination C existing in the extending portion 112.

Further, the extending portion 112 and the branch tube 114 are integrally formed, so that the blood bag system 10 can guide the plasma and the red blood cell contamination C to the branch tube 114 without leaking these components to an outside.

Further, the extending portion 112 and the branch tube 114 are held in the horizontal direction by the cassette 34, so that the centrifugal force can be favorably transferred to the red blood cell contamination C and movement can be encouraged when the centrifugal force is applied to the extending portion 112 and the branch tube 114. That is, the red blood cell contamination C is horizontally moved under an action of the centrifugal force and is easily moved in the radially outward direction A1, and thus can be more smoothly moved to the branch tube 114.

Note that the blood bag system 10 according to the present invention is not limited to the above-describe embodiment, and it is apparent that various configurations can be employed. Hereinafter, some modifications of the present invention will be described. Note that, in the description below, the same configurations and configurations having the same functions as the blood bag system 10 according to the present embodiment are denoted with the same reference signs, and detailed description is omitted.

Figure 8B:
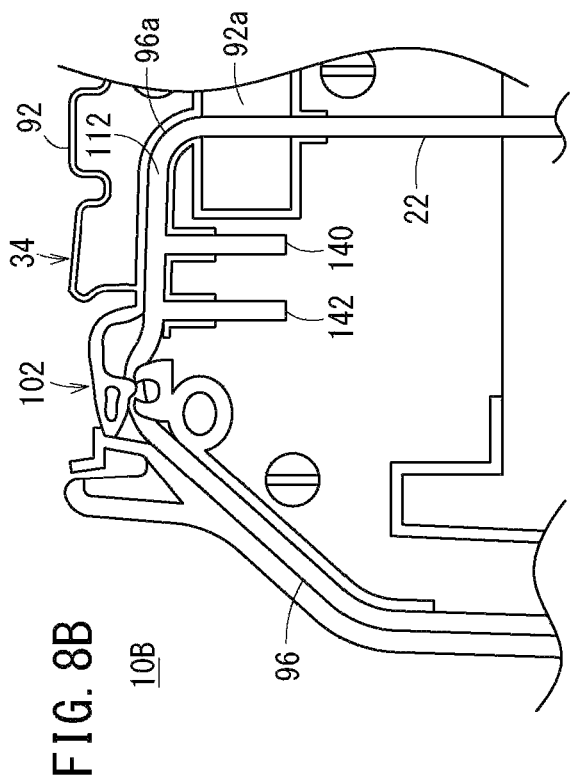
FIG. 8B is a plan view illustrating a storage portion of a blood bag system according to a second modification.
Figure 8D:
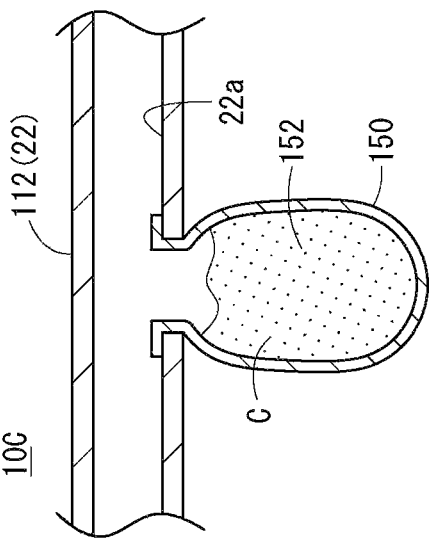
FIG. 8D is a sectional view illustrating a function of the storage portion of the blood bag system of FIG. 8C.
Figure 8A:
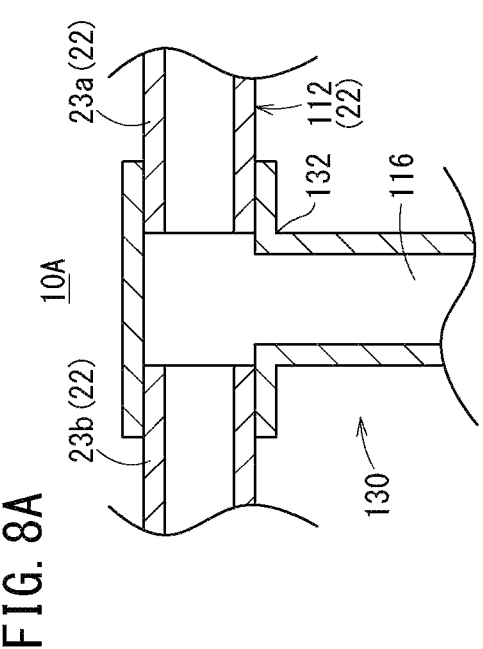
FIG. 8A is a sectional view illustrating a storage portion of a blood bag system according to a first modification.

A blood bag system 10A according to a first modification has a configuration in which, as illustrated in FIG. 8A, a first tube 22 is separated into an upstream tube 23a and a down-stream tube 23b in an extending portion 112, and these tubes are connected with a connection end 132 of a branch tube 130 formed into a T shape. As described above, the branch tube 130 may be formed as a separate member from the extending portion 112. Accordingly, an assembly method of blocking the linear first tube 22, and inserting the branch tube 130 to the blocked portion can be employed, and the branch tube 130 can be easily provided after the first tube 22 is installed in the cassette 34.

A blood bag system 10B according to a second modification has a configuration in which, as illustrated in FIG. 8B, two branch tubes 140 and 142 are provided to an extending portion 112. The two branch tubes 140 and 142 are provided in mutually separated positions. For example, the first branch tube 140 is provided in a position near an opening portion 92a, and the second branch tube 142 is provided in a position near the first clamp mechanism 102. By including of these two branch tubes 140 and 142, the blood bag system 10 can favorably store red blood cell contamination C. In short, the number of formation of the branch tubes provided in the extending portion 112 is not especially limited.

Figure 8C:
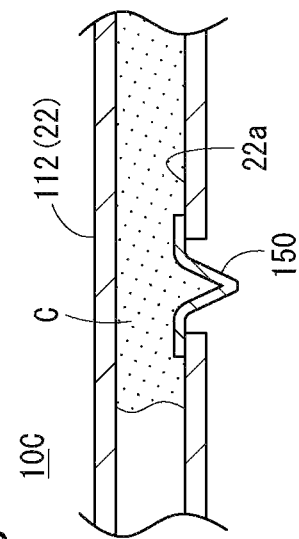
FIG. 8C is a sectional view illustrating a storage portion of a blood bag system according to a third modification.

A blood bag system 10C according to a third modification has a configuration in which, as illustrated in FIGS. 8C and 8D, a film member 150 (storage portion) elastically stretchable to a surface of an radially outward direction A1 side, of an extending portion 112 of a first tube 22. The film member 150 has a configuration to be expanded in a centrifugal direction as a fluid in the extending portion 112 is subject to centrifugal force, and can vary a volume of an internal storage space 152. Therefore, the film member 150 is in a shrunk state before centrifugal separation, as illustrated in FIG. 8C, and when red blood cell contamination C existing in the extending portion 112 is subject to the centrifugal force, the red blood cell contamination C is stored in the storage space 152, and the film member 150 is expanded in the radially outward direction A1. As described above, even when the storage portion is configured from the film member 150, the red blood cell contamination C can be favorably stored. Further, if the storage portion (film member 150) is configured to be deformed, an installation location of the storage portion on a cassette 34 can be freely set.

Figure 9A:
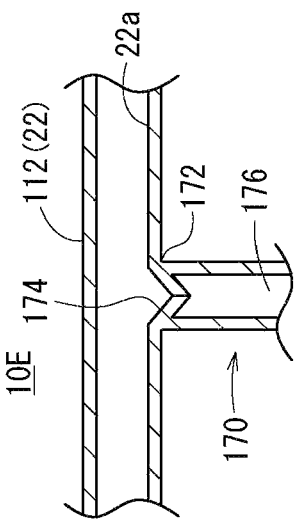
FIG. 9A is a sectional view illustrating a storage portion of a blood bag system according to a fourth modification.

A blood bag system 10D according to a fourth modification has a configuration in which, as illustrated in FIG. 9A, a connection end 162 of an extending portion 112 and a branch tube 160 is narrow, and the branch tube 160 is enlarged in an extending direction. When the branch tube 160 is formed as described above, red blood cell contamination C moved in a storage space 164 of a branch tube 160 can be prevented from flowing out to the extending portion 112 again.

Figure 9B:
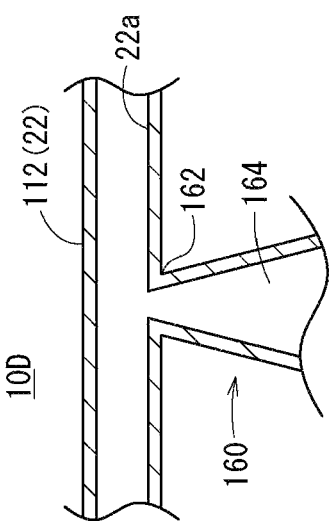
FIG. 9B is a sectional view illustrating a storage portion of a blood bag system according to a fifth modification.

A blood bag system 10E according to a fifth modification has a configuration in which, as illustrated in FIG. 9B, a valve portion 174 is provided inside a connection end 172 of a branch tube 170. The valve portion 174 has a function of a check valve, and is opened by red blood cell contamination C subject to centrifugal force, and can allow the red blood cell contamination C to flow into a storage space 176 of the branch tube 170. Meanwhile, even if the red blood cell contamination C flowing into the storage space 176 tries to flow out to the extending portion 112 again, the valve portion 174 is closed, so that the outflow of the red blood cell contamination C is blocked.

Figure 9C:
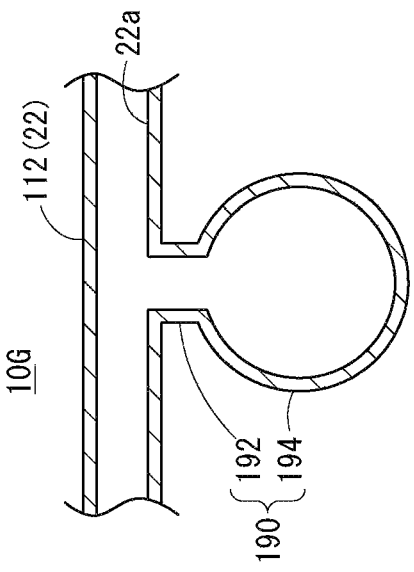
FIG. 9C is a sectional view illustrating a storage portion of a blood bag system according to a sixth modification.
Figure 9D:
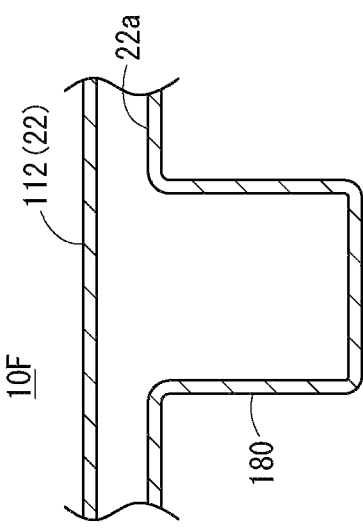
FIG. 9D is a sectional view illustrating a storage portion of a blood bag system according to a seventh modification.

In a blood bag system 10F according to a sixth modification, as illustrated in FIG. 9C, a storage portion of red blood cell contamination C is formed into a bag portion 180 relatively widely open in an extending direction of an extending portion 112. Further, a blood bag system 10G according to a seventh modification is formed into, as illustrated in FIG. 9D, a bag portion 190 including a neck portion 192 with a small diameter and an accumulation portion 194 having a relatively large volume. Even when a storage portion is formed as the bag portion 180 or 190 as described above, red blood cell contamination C can be stored. In short, the shape of the storage portion that stores the red blood cell contamination C is not especially limited, and various configurations can be employed.

Favorable embodiments have been described about the present invention. However, the present invention is not limited to the above embodiments, and it is apparent that various changes can be made without departing from the gist of the present invention. For example, in a blood bag system, each bag or tube can be attached to a blood product device without using a cassette. In this case, a similar effect to the above embodiments can be obtained by appropriately providing of a branch tube (storage portion). Further, a storage portion that stores blood is not applied only to a tube that transfers plasma, and it is apparent that the storage portion can be applied to various tubes that are subject to centrifugal force.

The invention claimed is:

1. A blood bag system comprising:
   a blood bag to which centrifugal force is provided in a state where whole blood or a blood component is stored; and
   a tube configured to circulate a fluid centrifugally separated from the blood bag, wherein
   the tube includes an extending portion extending in an approximately perpendicular direction to a centrifugal direction into which the centrifugal force is applied, and
   a storage portion configured to be able to store a fluid existing in the extending portion is provided at a side of the centrifugal direction of the extending portion.

2. The blood bag system according to claim 1, wherein the storage portion is a branch tube extending in the centrifugal direction.

3. The blood bag system according to claim 2, wherein the storage portion is a branch tube extending in the centrifugal direction;
   the blood bag and the tube are attached to a cassette at a time of providing of the centrifugal force, and the extending portion and the storage portion are held in a horizontal direction by the cassette.

4. The blood bag system according to claim 1, wherein the storage portion is deformed to have a space that is able to store the fluid by application of the centrifugal force to the fluid.

5. The blood bag system according to claim 4, wherein the storage portion is deformed to have a space that is able to store the fluid by application of the centrifugal force to the fluid;
the blood bag and the tube are attached to a cassette at a time of providing of the centrifugal force, and
the extending portion and the storage portion are held in a horizontal direction by the cassette.

6. The blood bag system according to claim 1, wherein the extending portion and the storage portion are integrally formed.

7. The blood bag system according to claim 6, wherein the extending portion and the storage portion are integrally formed;
the blood bag and the tube are attached to a cassette at a time of providing of the centrifugal force, and
the extending portion and the storage portion are held in a horizontal direction by the cassette.

8. The blood bag system according to claim 1, wherein the blood bag and the tube are attached to a cassette at a time of providing of the centrifugal force, and
the extending portion and the storage portion are held in a horizontal direction by the cassette.

* * * * *